US00PP19612P2

(12) United States Plant Patent
Sanchez

(10) Patent No.: US PP19,612 P2
(45) Date of Patent: Dec. 30, 2008

(54) ***IMPATIENS* PLANT NAMED 'BALFIEPRO'**

(50) Latin Name: *Impatiens walleriana*
Varietal Denomination: Balfiepro

(75) Inventor: Carlos Mena Sanchez, Dulce Nombre de Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/895,116

(22) Filed: Aug. 23, 2007

(51) Int. Cl.
*A01H 5/00* (2006.01)

(52) U.S. Cl. ..... Plt./317
(58) Field of Classification Search ..... Plt./317
See application file for complete search history.

(56) References Cited

U.S. PATENT DOCUMENTS

PP14,983 P2 * 7/2004 Heffner ..... Plt./317

OTHER PUBLICATIONS

UPOV ROM GTITM Computer Database, GTI Jouve Retrieval Software 2008/02 Citation for 'Balfiepro'.*
Canada Plant Breeders' Rights application number 07–5868 filed Apr. 12, 2007. Published information from Canada Plant Breeders' Rights Office web site attached.

* cited by examiner

*Primary Examiner*—Wendy C. Haas
(74) *Attorney, Agent, or Firm*—Audrey Charles

(57) ABSTRACT

A new and distinct cultivar of *Impatiens* plant named 'Balfiepro', characterized by its double type light to medium pink-colored flowers-colored flowers, medium green and white-colored variegated foliage, and moderately vigorous, compact, and upright-mounded growth habit.

1 Drawing Sheet

Latin name of genus and species of plant claimed: *Impatiens walleriana.*
Variety denomination: 'Balfiepro'.

BACKGROUND OF THE INVENTION

The present invention relates to a new and distinct cultivar of *Impatiens* plant botanically known as *Impatiens walleriana* and hereinafter referred to by the cultivar name 'Balfiepro'.

The new *Impatiens* cultivar is a naturally occurring sport of FIESTA 'Pink Ruffle', U.S. Plant Pat. No. 9,616, characterized by its double type medium pink-colored flowers, medium green-colored foliage, and upright-mounded growth habit. The new cultivar was discovered as a side shoot and selected during December 2003 in a controlled greenhouse production environment at Cartago, Costa Rica.

Asexual reproduction of the new cultivar by terminal stem cuttings since December 2003 at Cartago, Costa Rica and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfiepro' as a new and distinct cultivar of *Impatiens* plant:

1. Double type, light to medium pink-colored flowers;
2. Medium green and white-colored variegated foliage; and
3. Moderately vigorous, compact, and upright-mounded growth habit.

Plants of the new cultivar differ from plants of the parent primarily in foliage color. In addition, plants of the new cultivar have a slightly lighter shade of flower color than plants of the parent.

Of the many commercially available *Impatiens* cultivars, the most similar in comparison to the new cultivar is Summer Ice Pink Ice, not patented. However, in side by side comparisons, plants of the new cultivar differ from plants of 'Pink Ice' in the following characteristics:

1. Plants of the new cultivar have a flower color different from plants of 'Pink Ice'; and
2. Plants of the new cultivar have a darker leaf variegation color than plants of 'Pink Ice'.

In addition, the new cultivar is similar in comparison to Rosebud™ Pink Improved, not patented. However, in side by side comparisons, plants of the new cultivar differ from plants of Rosebud™ Pink Improved in the following characteristics:

1. Plants of the new cultivar are shorter than plants of Rosebud™ Pink Improved;
2. Plants of the new cultivar have different flower and leaf colors from plants of Rosebud™ Pink Improved; and
3. Plants of the new cultivar have fewer flowers than plants of Rosebud™ Pink Improved.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfiepro'. The plants were grown in 4.5 inch pots for 8 weeks in a greenhouse at West Chicago, Ill.

DETAILED BOTANICAL DESCRIPTION

Figure 1:
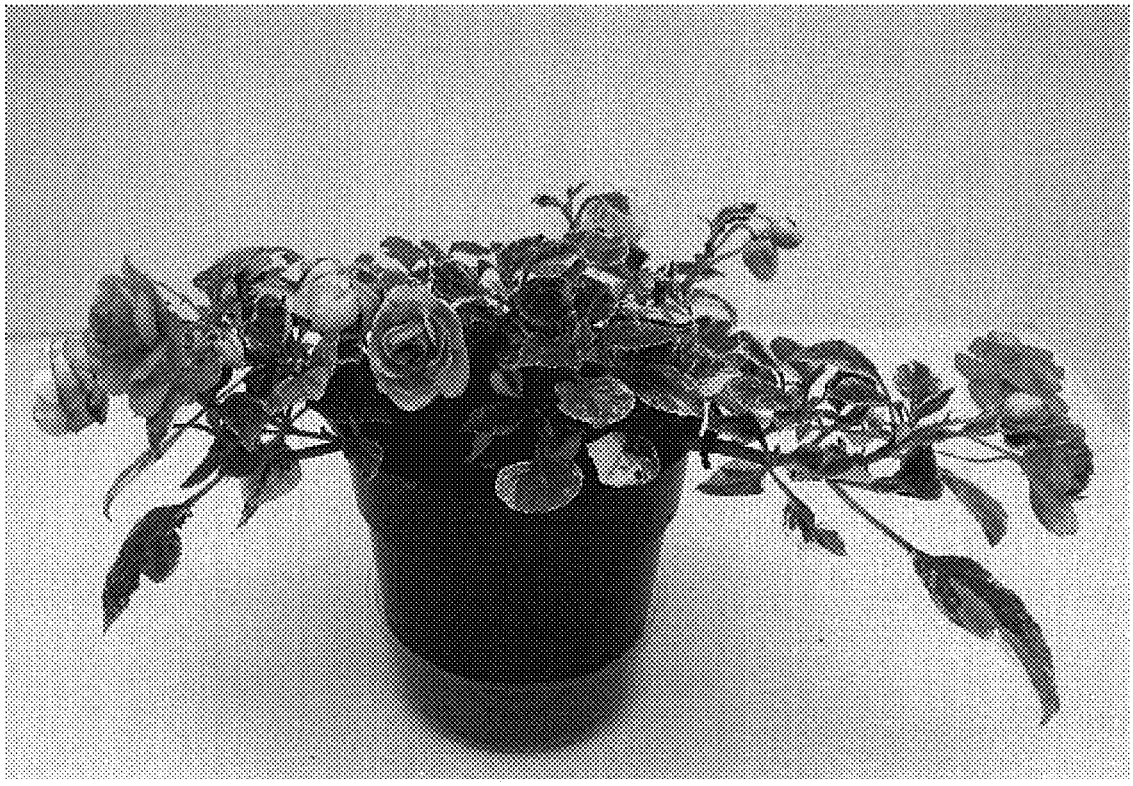
FIG. 1 illustrates a side view of the overall growth and flowering habit of 'Balfiepro'.
Figure 2:
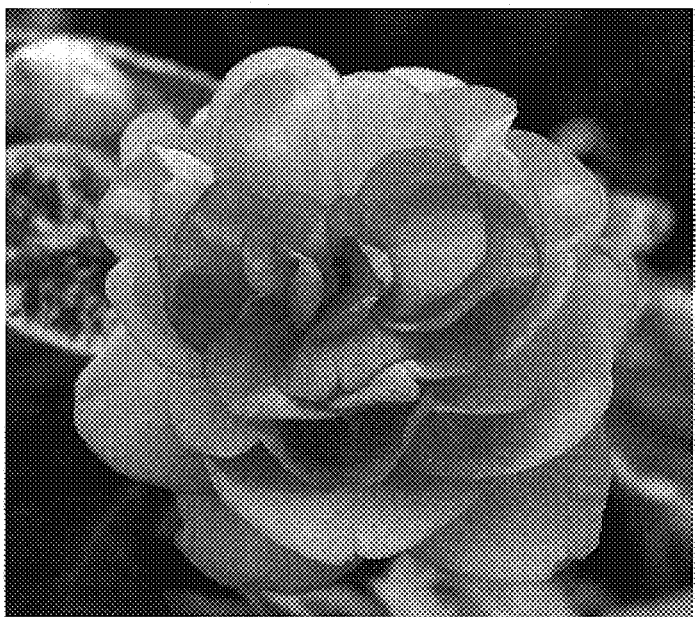
FIG. 2 illustrates a close-up view of an individual flower of 'Balfiepro'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Mar. 29, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens walleriana* cultivar Balfiepro.

Parentage:

*Parent.*—Fiesta Pink Ruffle, U.S. Plant Pat. No. 9,616.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, compact, and upright-mounded.

*Size.*—Height from soil level to top of plant plane: Approximately 8.3 cm. Width: Approximately 26.7 cm.

*Branching habit.*—Freely basal branching. Quantity of main branches per plant: Approximately 5.

*Branch.*—Strength: Moderately strong. Length: Approximately 10.6 cm. Diameter at central internode: Approximately 3.0 mm. Length of central internode: Approximately 1.2 cm. Texture: Glabrous. Color of young and mature stems: 146B with speckles of 185A.

Foliage description:

*General description.*—Quantity of leaves per main branch: Approximately 8. Fragrance: None. Form: Simple. Arrangement: Alternate.

*Leaves.*—Aspect: Acute angle to stem, becomes perpendicular with age. Shape: Ovate. Margin: Crenate, ciliate. Apex: Acute. Base: Attenuate. Venation pattern: Pinnate. Length of mature leaf at center of stem: Approximately 7.6 cm. Width of mature leaf at center of stem: Approximately 3.0 cm. Texture of upper and lower surfaces: Glabrous. Color of upper surface of young and mature foliage: Central area of N138C to N138A and variegated margins of 155A with venation indistinguishable from leaf. Color of lower surface of young and mature foliage: 138B and variegated margins of 155A with venation of 138A.

*Petiole.*—Length: Approximately 2.3 cm. Diameter: Approximately 2.0 mm. Texture: Glabrous. Color: 138B.

Flowering description:

*Flowering habit.*—'Balfiepro' is freely flowering under outdoor growing conditions with substantially continuous blooming from spring through autumn and year-round in greenhouse environment.

*Lastingness of individual flower on the plant.*—Approximately 4 to 6 days.

Flower description:

*General description.*—Type: Double. Quantity per plant: Approximately 5. Fragrance: None.

*Bud.*—Rate of opening: Generally takes 3 to 5 days for bud to progress from first color to fully open flower. Quantity showing color per plant: Approximately 4.

*Bud just before opening.*—Shape: Ovoid. Length: Approximately 1.4 cm. Diameter: Approximately 1.0 cm. Color: 62B.

*Corolla.*—Shape: Hemispherical. Width: Approximately 3.9 cm. Depth: Approximately 1.8 cm. Borne: Above and below the foliage.

*Petals.*—Quantity: 20. Shape: Obovate, innermost irregular. Aspect: Flat. Appearance: Iridescent. Margin: Entire. Apex: Obtuse, some are emarginate. Base: Attenuate. Length of outermost petals: Approximately 2.0 cm. Width of outermost petals: Approximately 1.7 cm. Length of innermost petals: Approximately 1.0 cm. Width of innermost petals: Approximately 7.6 mm. Texture of upper and lower surfaces: Glabrous. Color of upper surface when first and fully open: 55C with margins of 55A. Color of lower surface when first and fully open: 55D with margins of 55A.

*Spur.*—Quantity: 1 per flower. Length: Approximately 3.0 cm. Diameter at tip: Less than 1 mm. Diameter at base: Approximately 2.0 mm. Texture: Glabrous. Color: 145D with an overlay of 185D and tip of 145C.

*Peduncle.*—Strength: Moderately strong. Aspect: Acute angle to stem. Length: Approximately 3.4 cm. Diameter: Approximately 2.0 mm. Texture: Glabrous. Color: 145B.

*Sepals.*—Quantity per flower: 4 with one fused to base of upper petal. Shape of lateral sepals: Lanceolate. Shape of lower sepal: Ovate. Apex of all sepals: Acute. Length of lateral sepals: Approximately 2.0 mm. Width of lateral sepals: Approximately 1.0 mm. Length of lower sepal: Approximately 1.3 cm. Width of lower sepal: Approximately 9.0 mm. Texture of upper and lower surfaces of all sepals: Glabrous. Color of lateral sepals: 145D. Color of lower sepal: 62D.

*Reproductive organs.*—None observed.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfiepro', substantially as herein shown and described.

* * * * *